(12) United States Patent
Yamamoto et al.

(10) Patent No.: US 10,419,693 B2
(45) Date of Patent: Sep. 17, 2019

(54) IMAGING APPARATUS, ENDOSCOPE APPARATUS, AND MICROSCOPE APPARATUS

(71) Applicant: OLYMPUS CORPORATION, Tokyo (JP)

(72) Inventors: Eiji Yamamoto, Hachioji (JP); Hiroyuki Kamee, Koganei (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 197 days.

(21) Appl. No.: 15/238,341

(22) Filed: Aug. 16, 2016

(65) Prior Publication Data
US 2016/0360125 A1 Dec. 8, 2016

Related U.S. Application Data

(63) Continuation of application No. PCT/JP2015/051810, filed on Jan. 23, 2015.

(30) Foreign Application Priority Data

Feb. 19, 2014 (JP) ................................. 2014-029925

(51) Int. Cl.
*G02B 6/28* (2006.01)
*H04N 5/343* (2011.01)
(Continued)

(52) U.S. Cl.
CPC ......... *H04N 5/343* (2013.01); *A61B 1/00009* (2013.01); *A61B 1/045* (2013.01);
(Continued)

(58) Field of Classification Search
CPC ........ H04N 5/343; H04N 5/2256; H04N 9/07; H04N 5/238; H04N 2005/2255;
(Continued)

(56) References Cited

U.S. PATENT DOCUMENTS

2002/0013531 A1* 1/2002 Hayashi ............. A61K 49/0034
600/476
2010/0245551 A1* 9/2010 Morita ............... A61B 1/00009
348/68
(Continued)

FOREIGN PATENT DOCUMENTS

EP 2 859 837 A1 4/2015
JP 63-227293 A 9/1988
(Continued)

OTHER PUBLICATIONS

International Search Report dated Mar. 31, 2015 issued in corresponding Japanese Patent Application No. PCT/JP2015/051810.
(Continued)

*Primary Examiner* — Howard D Brown, Jr.
(74) *Attorney, Agent, or Firm* — Scully, Scott, Murphy & Presser, P.C.

(57) ABSTRACT

An imaging apparatus includes an illumination section, an imaging section, and an image processor. The illumination section includes an illumination unit configured to selectively emit illumination light rays of light wavelength bands different from each other, and an illumination switch controller which generates an illumination unit control signal corresponding to each of sets of emission patterns so that combinations of the light wavelength bands of the illumination light rays emitted from the illumination unit are different from each other and the illumination switch controller controlling the illumination unit so that the illumination light rays are sequentially emitted from the illumination unit in the sets of emission patterns different from each other.

22 Claims, 6 Drawing Sheets

(51) Int. Cl.
*A61B 1/06* (2006.01)
*G02B 21/06* (2006.01)
*G03B 15/02* (2006.01)
*H04N 5/238* (2006.01)
*H04N 9/07* (2006.01)
*G02B 21/36* (2006.01)
*G02B 23/24* (2006.01)
*H04N 5/225* (2006.01)
*G03B 33/00* (2006.01)
*G02B 23/26* (2006.01)
*A61B 1/00* (2006.01)
*A61B 1/045* (2006.01)
*A61B 1/05* (2006.01)

(52) U.S. Cl.
CPC ............... *A61B 1/05* (2013.01); *A61B 1/06* (2013.01); *A61B 1/0638* (2013.01); *G02B 21/06* (2013.01); *G02B 21/365* (2013.01); *G02B 23/2461* (2013.01); *G02B 23/2484* (2013.01); *G02B 23/26* (2013.01); *G03B 15/02* (2013.01); *G03B 33/00* (2013.01); *H04N 5/2256* (2013.01); *H04N 5/238* (2013.01); *H04N 9/07* (2013.01); *H04N 2005/2255* (2013.01)

(58) Field of Classification Search
CPC ............... G02B 23/2461; G02B 23/26; G02B 23/2484; G02B 21/365; G02B 21/06; A61B 1/0009; A61B 1/045; A61B 1/0638; A61B 1/05; A61B 1/06; G03B 33/00; G03B 15/02
See application file for complete search history.

(56) References Cited

U.S. PATENT DOCUMENTS

2013/0338438 A1* 12/2013 Watanabe .............. A61B 1/043
                                                                    600/109
2015/0092035 A1*  4/2015 Yamamoto ............ G02B 21/06
                                                                    348/68
2015/0185421 A1*  7/2015 Leavesley .............. G01N 21/55
                                                                    356/445
2016/0360125 A1* 12/2016 Yamamoto ............. A61B 1/06

FOREIGN PATENT DOCUMENTS

| | | |
|---|---|---|
| JP | 2010-042133 A | 2/2010 |
| JP | 2013-248319 A | 12/2013 |
| JP | 2013-255655 A | 12/2013 |
| WO | 2013/187215 A1 | 12/2013 |

OTHER PUBLICATIONS

International Preliminary Report on Patentability together with the Written Opinion from related International Application No. PCT/JP2015/051810 dated Sep. 1, 2016.

Chinese Office Action dated Mar. 3, 2017 in Chinese Patent Application No. 201580008463.5.

Japanese Office Action dated Mar. 13, 2018 in Japanese Patent Application No. 2014-029925.

German Office Action dated Jun. 24, 2019 in German Patent Application No. 11 2015 000 863.2.

* cited by examiner

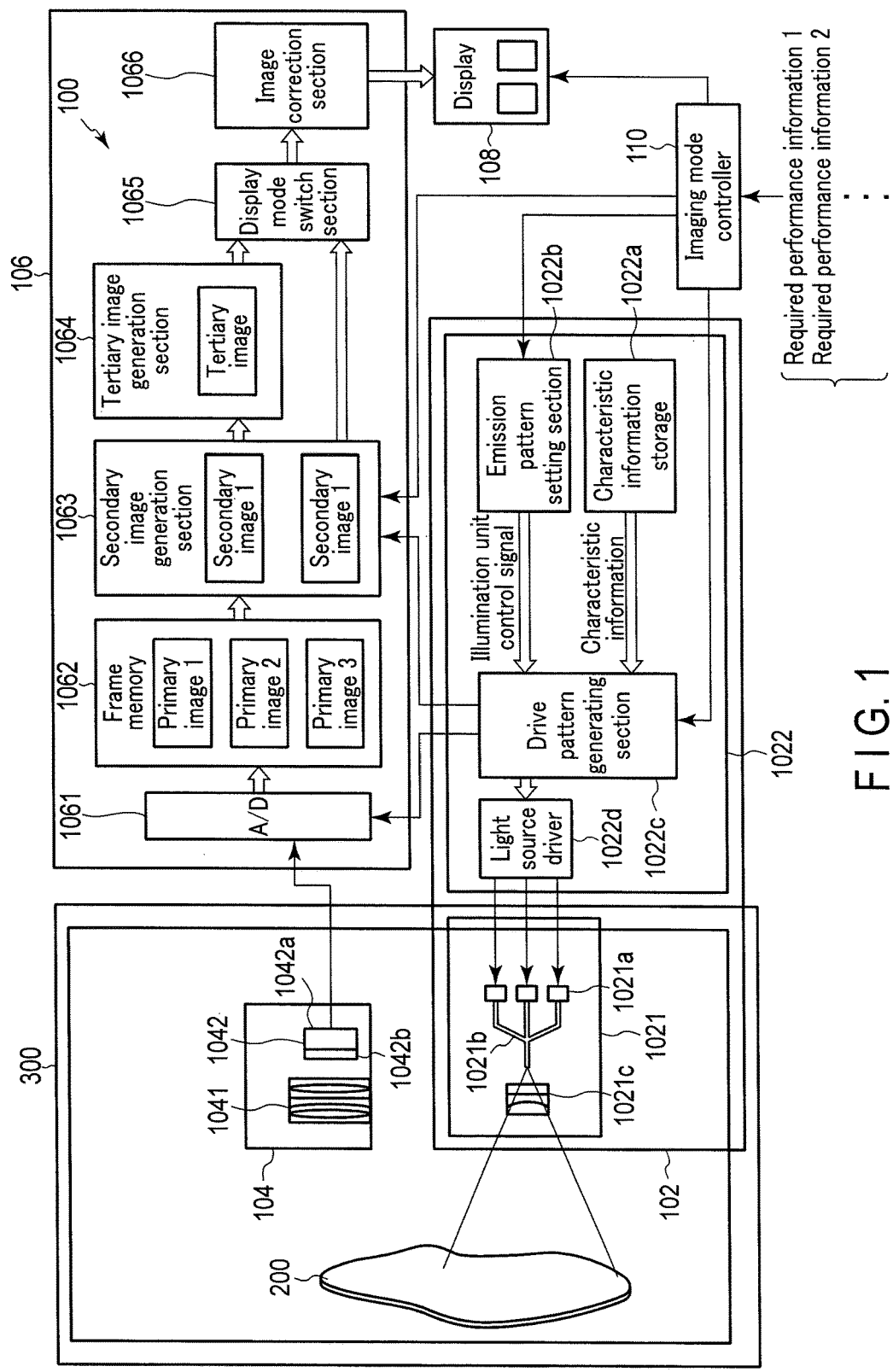
F I G. 1

| Configuration | a | b |
|---|---|---|
| Number of light wavelength bands emittable by light source unit | 3 | 3 |
| Number of light wavelength bands emitted by one pair of emission patterns | 3 | 3 |
| Number of emission patterns | 1 | 1 |
| Illumination method | 3-band simultaneous illumination | |
| Emission patterns | $t=t1$ B G R<br>$t=t2$ B G R<br>$t=t3$ B G R | |
| Filter | Primary colors | Complementary colors |
| State where emission patterns enter pixels | (Display frames 1, 2, 3 with R G B pixels) | (Display frames 1, 2, 3 with R G B pixels) |
| Number of display frames composed for N=3 emission patterns | 3 | 3 |
| Resolution (number of pixels managed by one light receiving element) | 1 | 1 |
| Light receiving amount/ (pixels, frames) | 1 | 2 |
| Average velocity of frame display | 1 | 1 |

FIG. 2

| Configuration | c |
|---|---|
| Number of light wavelength bands emittable by light source unit | 3 |
| Number of light wavelength bands emitted by one pair of emission patterns | 1 |
| Number of emission patterns | 3 |
| Illumination method | 1 band/pattern switch illumination |
| Emission patterns | $t=t1$ R, $t=t2$ G, $t=t3$ B |
| Filter | None |
| State where emission patterns enter pixels | Primary image 1 (R R R), Primary image 2 (G G G), Primary image 3 (B B B) → Secondary image → display frame |
| Number of display frames composed for N=3 emission patterns | 3 |
| Resolution (number of pixels managed by one light receiving element) | 3 |
| Light receiving amount/ (pixels, frames) | 1 |
| Average velocity of frame display | 1/3 |

FIG. 3

| Configuration | d | e |
|---|---|---|
| Number of light wavelength bands emittable by light source unit | 3 | 3 |
| Number of light wavelength bands emitted by one pair of emission patterns | 2 (3 in some pairs) | 2 (3 in some pairs) |
| Number of emission patterns | 3 (or 4) | 3 (or 4) |
| Illumination method | Switch of 2 bands/patterns | Switch of 2 bands/patterns |
| Emission patterns | Pattern sets A1 to A3<br>t=t1: B, G at λ1, λ2 — Pattern A1<br>t=t2: B, R at λ1, λ3 — Pattern A2<br>t=t3: G, R at λ2, λ3 — Pattern A3 | Pattern sets A1 to A3<br>t=t1: B, G at λ1, λ2 — Pattern A1<br>t=t2: B, R at λ1, λ3 — Pattern A2<br>t=t3: G, R at λ2, λ3 — Pattern A3 |
| Light receiving element filter | None | Primary colors |
| State where emission patterns enter pixels | (diagram: Primary images 1, 2, 3 → Secondary image) | (diagram: Secondary image 1, Secondary image 2) |
| Number of display frames composed for N=3 emission patterns | 1 (secondary image) | 2 (secondary image) |
| Resolution (number of pixels managed by one light receiving element) | 3 | 1 |
| Light receiving amount/(pixels, frames) | 1/3 | 1/2 |
| Average velocity of frame display | 2 | 1 |

FIG. 4

| Configuration | f1 | f2 | f3 | f4 | f5 | f6 |
|---|---|---|---|---|---|---|
| Number of light wavelength bands emittable by light source unit | | | 3 | | | |
| Number of light wavelength bands emitted by one pair of emission patterns | | | 2 (3 in some pairs) | | | |
| Number of emission patterns | | | 3 (or 4) | | | |
| Illumination method | | Add full band/pattern as needed on basis of switch illumination of 2 bands/patterns | | | | |
| Emission patterns | Pattern sets A1 to A3 — t=t1, t=t2, t=t3 Light intensity patterns (B,G / B,R / G,R at λ1,λ2,λ3) Pattern A1, Pattern A2, Pattern A3 | | | Pattern sets A0 to A3 — t=t0, t=t1, t=t2, t=t3 Light intensity (B,G / B,G / B / G at λ) Pattern A0, Pattern A1, Pattern A2, Pattern A3 | | |
| Light receiving element filter | | | | Complementary colors | | |
| State where emission patterns enter pixels | (Secondary image 1 / Primary image 2 / Secondary image 2 diagrams with R,G,B pixel arrays) | | | (Secondary image 1 / Secondary image 2 / Secondary image 3 diagrams with R,G,B pixel arrays) | | |
| Number of display frames composed for N=3 emission patterns | 3 (Secondary image) | 1 (Tertiary image) | Switch between secondary image and tertiary image at proper time | 3 (Secondary image) | 1 (Tertiary image) | Switch between secondary image and tertiary image at proper time |
| Resolution (number of pixels managed by one light receiving element) | 1 | 3 | 3 or 1 | 1 | 3 | 3 or 1 |
| Light receiving amount/(pixels, frames) | 4/3 | 4/3 | 4/3 | 4/3 | 4/3 | 4/3 or 4/3 |
| Average velocity of frame display | 1 | 1/3 | 1 or 1/3 | 1 | 1/3 | 1 or 1/3 |

FIG. 5

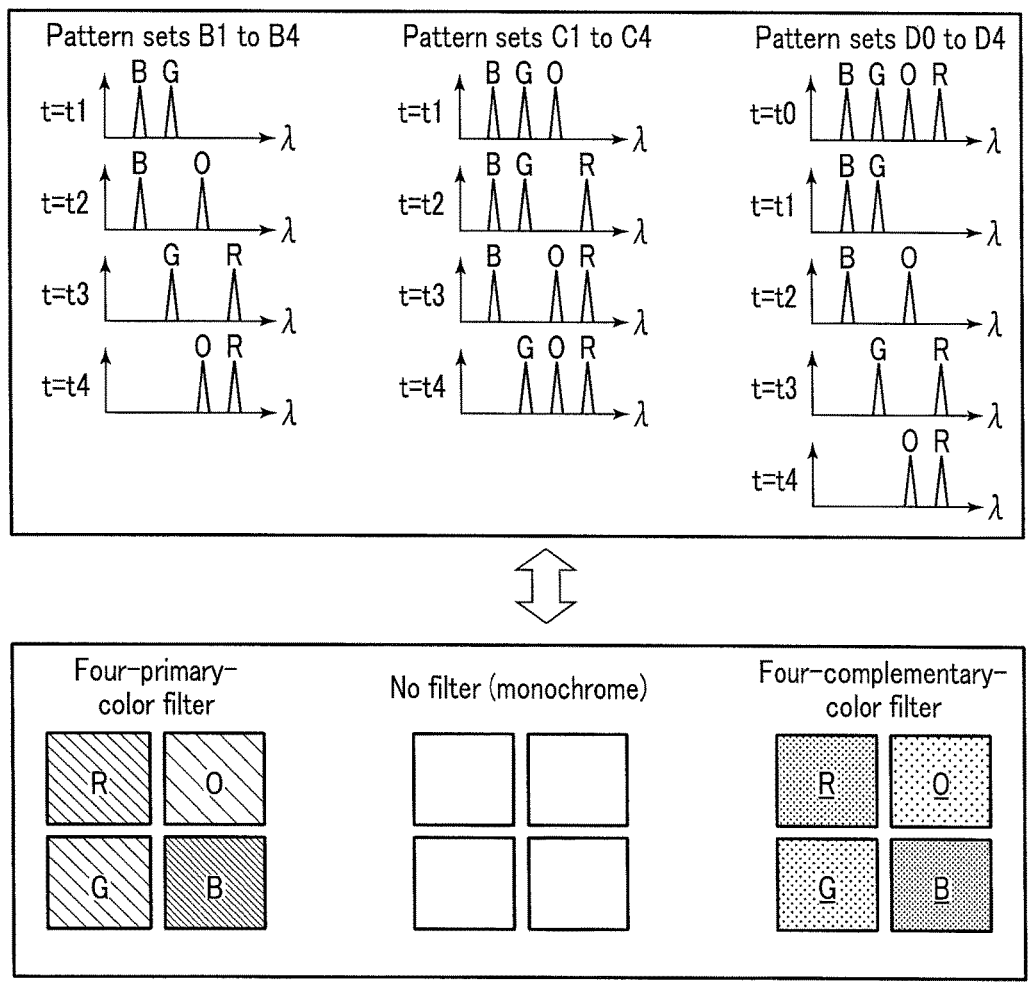
F I G. 6

IMAGING APPARATUS, ENDOSCOPE APPARATUS, AND MICROSCOPE APPARATUS

CROSS-REFERENCE TO RELATED APPLICATIONS

This application is a Continuation Application of PCT Application No. PCT/JP2015/051810, filed Jan. 23, 2015 and based upon and claiming the benefit of priority from the prior Japanese Patent Application No. 2014-029925, filed Feb. 19, 2014, the entire contents of both of which are incorporated herein by reference.

BACKGROUND OF THE INVENTION

1. Field of the Invention

The present invention relates to an imaging apparatus, an endoscope apparatus, and a microscope apparatus.

2. Description of the Related Art

As a method of colorizing images, there has heretofore been known a general method which colorizes images by a combination of illumination light (e.g. white light) having a broad light wavelength and an image pickup device in which color filters are provided on light receiving elements (such a method will be hereinafter referred to as a white light broadband illumination method). As a method of colorizing images by using an image pickup device having no color selectivity in which no color filters are provided on light receiving elements, there has also been known a method suggested in Jpn. Pat. Appln. KOKAI Publication No. 63-227293 to apply different monochromatic illumination lights to an observation target field by field and synchronize signals sequentially obtained from the image pickup device field by field to obtain a color image (such a method will be hereinafter referred to as a frame sequential illumination method).

BRIEF SUMMARY OF THE INVENTION

An imaging apparatus according to an aspect of the invention comprises: an illumination section comprising a light source drive circuit which drives a light source to apply an illumination light ray to an observation target; an imaging section which comprises an image pickup device where imaging pixels having a predetermined arrangement and having predetermined light wavelength sensitivity characteristics are disposed, the imaging section being configured to image the observation target by the image pickup device to acquire an image signal regarding the observation target; and an image processor which processes the image signal, wherein the illumination section comprises an illumination unit configured to selectively emit illumination light rays of light wavelength bands different from each other, and an illumination switch controller which generates an illumination unit control signal corresponding to each of sets of emission patterns so that combinations of the light wavelength bands of the illumination light rays emitted from the illumination unit are different from each other based on arrangement information in the light wavelength sensitivity characteristics of the imaging pixels of the imaging section and required performance information, the illumination switch controller controlling the illumination unit so that the illumination light rays are sequentially emitted from the illumination unit in the sets of emission patterns different from each other by switching of the illumination unit control signal, and the image processor processes the image signal based on the illumination unit control signal and the arrangement information in the light wavelength sensitivity characteristics of the imaging pixels of the imaging section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing the overall configuration of an imaging apparatus according to one embodiment of the present invention;

FIG. 2 is a table showing a (configuration a) and a (configuration b);

FIG. 3 is a table showing a (configuration c);

FIG. 4 is a table showing a (configuration d) and a (configuration e);

FIG. 5 is a table showing a (configuration f); and

FIG. 6 is a diagram showing a modification of one embodiment of the present invention.

DETAILED DESCRIPTION OF THE INVENTION

Hereinafter, embodiments of the present invention will be described with reference to the drawings. FIG. 1 is a diagram showing the overall configuration of an imaging apparatus according to one embodiment of the present invention. An imaging apparatus 100 shown in FIG. 1 includes an illumination section 102, an imaging section 104, an image processor 106 (an image processing section), a display 108 (a display section), and an imaging mode controller 110. This imaging apparatus 100 basically applies illumination light rays to an observation target 200 from the illumination section 102, images the light ray reflected and scattered by the observation target in the imaging section 104, and processes an image signal obtained by the imaging section 104 in the image processor 106. This imaging apparatus 100 then causes the display 108 to display an image obtained by the processing in the image processor 106.

The illumination section 102 applies the illumination light rays to the observation target 200. This illumination section 102 includes an illumination unit 1021 and an illumination switch controller 1022 (an illumination switch control unit).

The illumination unit 1021 is configured to selectively apply illumination light rays of L different light wavelength bands. In the present embodiment, L is, for example, 3 or more. The illumination unit 1021 as an example has light sources 1021a, a waveguide 1021b, and a light distribution lens 1021c. The light sources 1021a are L light sources having different light wavelength bands, and are, for example, semiconductor lasers (LD) or superluminescent diodes (SLD). L is 3 in the example shown in FIG. 1, and the three light sources 1021a shown in FIG. 1 emit red (R), green (G), and blue (B) illumination light rays, respectively. The waveguide 1021b is, for example, an optical fiber, and is optically coupled to the L light sources 1021a. This waveguide 1021b multiplexes the illumination light rays emitted from the light sources 1021a, and brings the multiplexed light rays out to the light distribution lens 1021c. The light distribution lens 1021c is, for example, a planoconcave lens, and shapes the illumination light rays emitted from the waveguide 1021b into a predetermined light distribution spread angle and then applies the illumination light rays to the observation target 200.

The illumination switch controller 1022 includes a characteristic information storage 1022a (a characteristic information storage section), an emission pattern setting section 1022b (an emission pattern setting circuit), a drive pattern generating section 1022c (a drive pattern generating circuit), and a light source driver 1022d, and controls the illumination unit 1021 so that illumination light rays of predetermined N sets of emission patterns are emitted from the light sources 1021a. The emission patterns are patterns indicating combinations of light rays of M light wavelength bands extracted by the respective timings: times t1, t2, ..., tN. Here, M is an integer equal to or more than 2 and less than or equal to L, and N is an integer equal to or more than 2. In addition, emission intensities and emission times of the illumination light rays may be included in the emission patterns. The characteristic information storage 1022a stores characteristic information for the illumination section 102 and the imaging section 104. The characteristic information for the illumination section 102 includes, for example, information regarding connection terminals of the light sources 1021a and the light source driver 1022d, information regarding colors (wavelength bands) that can be emitted by the light sources 1021a, and information regarding the correspondence between the drive intensities of the light sources 1021a and the outputs of the light sources 1021a. The characteristic information for the imaging section 104 is mainly information regarding the arrangement of light wavelength sensitivity characteristics of imaging pixels that constitute the imaging section, and includes, for example, information indicating the presence of color filters of an image pickup device 1042 which will be described later, and information indicating the kinds of color filters and their arrangement. The emission pattern setting section 1022b sets N sets of emission patterns in accordance with the input of required performance information for the imaging apparatus 100 from the imaging mode controller 110 so that color combinations of the illumination light rays are different, and the emission pattern setting section 1022b generates an illumination unit control signal in accordance with the set emission patterns. The required performance information is information to determine the performance of the imaging apparatus 100, for example, whether to set the imaging apparatus 100 to a high frame rate mode, a high resolution mode, or a high sensitivity mode. The drive pattern generating section 1022c generates a light source driver control signal so that the illumination light rays having the emission patterns set in the emission pattern setting section 1022b will be emitted from the light sources 1021a on the basis of the characteristic information for the illumination section 102 and the illumination unit control signal. The light source driver 1022d controls the driving of the light sources 1021a of the illumination unit 1021 in accordance with the light source driver control signal. The illumination switch controller 1022 includes electronic circuits configured to process some kinds of signals.

By having the illumination unit 1021 and the illumination switch controller 1022 described above, the illumination section 102 can extract light rays of predetermined M light wavelength bands and emit the extracted illumination light rays at a predetermined time. The illumination section 102 also changes combinations of the extracted illumination light rays of the predetermined M light wavelength bands into N combinations and then emits illumination light rays to the observation target 200. Here, L is the number of bands of light wavelength that can be emitted by the illumination unit, M is the number of light wavelength bands to be emitted in one set of emission patterns, and N is the number of emission patterns to be repeatedly emitted.

The imaging section 104 images the observation target to obtain an image signal regarding the observation target. The imaging section 104 includes an image formation lens 1041 and the image pickup device 1042. The image formation lens 1041 is an optical system which forms the light ray, for example, reflected and scattered by the observation target 200 into an image on the image pickup device 1042. The image pickup device 1042 converts an optical image formed via the image formation lens 1041 into an image signal as an electric signal. The image pickup device 1042 has light receiving elements 1042a and color filters 1042b. The light receiving elements 1042a are, for example, two-dimensionally arranged photodiodes, and perform photoelectric conversion. The color filters 1042b are provided on the light receiving elements 1042a to correspond to the respective light receiving elements 1042a, and allow an optical image of a particular wavelength band of the light rays from the observation target 200 to enter the light receiving elements 1042a. Although described later in detail, the image pickup device 1042 has no color filters 1042b in some cases. In this case, the image pickup device 1042 has no color selectivity.

The imaging apparatus 100 in the present embodiment can most ideally bring out its performance under an observation environment in which the illumination light rays from the illumination section 102 alone are applied to the observation target 200, that is, under an environment in which there is substantially no influence of outside light ray. Therefore, the imaging apparatus 100 in the present embodiment is preferably used under an environment in which the influence of outside light ray other than the illumination light rays from the illumination section 102 is inhibited, for example, used in an outside light inhibiting component 300 which is configured to cover the illumination section 102, the imaging section 104, and the observation target 200. When the illumination section 102, the imaging section 104, and the observation target 200 cannot be disposed in the outside light inhibiting component 300, it is preferable to cancel the influence of the outside light ray on the image signal at the stage of image processing to obtain image signals by the emission patterns. Thus, the imaging apparatus 100 in the present embodiment is suitable to a microscope apparatus and an endoscope apparatus which often acquire images under an environment in which there is substantially no influence of outside light ray.

λLw, i and λFw, i preferably satisfy the condition of (Equation 1) below:

$$\lambda Lw, i < \lambda Fw, i \quad (i=1,2,\ldots,L) \tag{1}$$

wherein λLw, i (i=1, 2, ..., L) is the wavelength band width of the light rays of L wavelength bands that can be emitted by the illumination unit 1021, and λFw, i (i=1, 2, ..., L) is the wavelength band width of the color filters 1042b provided in the image pickup device 1042.

The spectral widths of the illumination light rays are preferably small to well satisfy the condition of Equation (1). Therefore, the light sources 1021a are suitably laser light sources or superluminescent diodes. As long as the condition of Equation (1) can be satisfied, color reproducibility does not decrease even if the number M of light wavelength bands in each emission pattern increases. It is also possible to provide high image display performance (e.g. resolution, a frame rate, an S/N ratio, and color reproducibility) corresponding to the number M of light wavelength bands.

The image processor 106 processes the image signal obtained in the imaging section 104 to generate an image. The image processor 106 in the present embodiment performs various processing in accordance with the characteristics of the light sources 1021a, the characteristics of the image pickup device 1042, and functional requirements of image processing. FIG. 1 shows a typical configuration of the image processor 106. The image processor 106 in FIG. 1 includes an A/D converter 1061, a frame memory 1062, a secondary image generation section 1063 (a secondary image generation circuit), a tertiary image generation section 1064 (a tertiary image generation circuit), a display mode switch section 1065 (a display mode switch circuit), and an image correction section 1066 (an image correction circuit). The image processor 106 includes electronic circuits configured to process some kinds of signals.

The A/D converter 1061 samples the image signal obtained in the imaging section 104 synchronously with the input timing of a light source driver control signal generated in the drive pattern generating section 1022c, and converts the sampled image signal into an image signal (primary image information) which is a digital signal. The frame memory 1062 stores the primary image information obtained in the A/D converter 1061. In the present embodiment, N times of imaging corresponding to N sets of emission patterns are performed to obtain N pieces of primary image information. The frame memory 1062 stores each of the N pieces of primary image information. The secondary image generation section 1063 subjects the N pieces of primary image information stored in the frame memory 1062 to processing corresponding to the light source driver control signal generated in the drive pattern generating section 1022c to generate secondary image information. The tertiary image generation section 1064 processes the secondary image information as needed to generate tertiary image information. Details of the processing in the secondary image generation section 1063 and the tertiary image generation section 1064 will be described later. The display mode switch section 1065 switches the image information to be output to the image correction section 1066 between the secondary image information generated in the secondary image generation section 1063 and the tertiary image information generated in the tertiary image generation section 1064 in accordance with the display mode of the display 108. The image correction section 1066 subjects the secondary image information or the tertiary image information to correction processing necessary for display and recording. This correction processing is, for example, a correction of color temperature, a correction of gamma characteristics, and emphasizing processing or suppressing processing for a particular light wavelength (a color component in the image information).

The display 108 displays a display frame based on at least one of the secondary image information and the tertiary image information corrected by the image correction section 1066. That is, the display 108 independently displays the display frame based on the secondary image information and the display frame based on the tertiary image information, or simultaneously displays the display frame based on the secondary image information and the display frame based on the tertiary image information. It is determined which display is performed on the basis of the display mode. The display mode is set by, for example, a user.

The imaging mode controller 110 is, for example, a CPU, and inputs synchronization signals to the image pickup device 1042 of the imaging section 104, the drive pattern generating section 1022c of the illumination section 102, the secondary image generation section 1063 of the image processor 106, and the display 108 to synchronously control these sections. The imaging mode controller 110 also inputs required performance information to the emission pattern setting section 1022b. The required performance information is set by, for example, the user.

The imaging apparatus 100 basically has the configuration shown in FIG. 1. However, the imaging apparatus 100 is classified into six configurations, that is, a (configuration a), a (configuration b), a (configuration c), a (configuration d), a (configuration e), and a (configuration f) by how the emission patterns are set, the presence of the color filters 1042b to be combined with the light receiving elements 1042a, and the kinds of color filters 1042b, and the imaging apparatus 100 performs different operations depending on the respective configurations. The operation corresponding to each configuration of the imaging apparatus 100 is described below. Here, in the following explanation, the total time from the beginning of an illumination operation to the acquisition a necessary number of primary images to generate a final display frame image (secondary image or tertiary image) is referred to as an "image extraction time", and its velocity is referred to as an "average velocity of frame display". A high "average velocity of frame display" means that the delay of the display of a moving observation target is small, that is, the frame rate is high and the motion of the observation target can be naturally (smoothly) displayed. Contrarily, a low "average velocity of frame display" means that the delay of the display of a moving observation target is large, that is, the frame rate is low, the time interval up to the switch of display is long, and the motion of the observation target cannot be smoothly displayed.

First, the (configuration a) and the (configuration b) are described with reference to FIG. 2. The (configuration a) and the (configuration b) are configurations that use the emission patterns corresponding to the white light broadband illumination method. In the white light broadband illumination method, the emission pattern setting section 1022b sets an emission pattern so that the illumination light rays of L light wavelength bands are simultaneously applied to the observation target 200 in each timing. Therefore, L=M, and N=1. In the following explanation, the illumination unit 1021 can emit the illumination light rays of three RGB colors. In this case, L=3, M=3, and N=1, as shown in FIG. 2.

There is a difference of the kinds of color filters 1042b between the (configuration a) and the (configuration b). That is, the color filters 1042b in the (configuration a) are primary color filters, and the color filters 1042b in the (configuration b) are complementary color filters. The "primary color filters" in the present embodiment are configured so that filter elements are two-dimensionally arranged to correspond to the positions of the light receiving elements, the filter elements transmitting light wavelength band of incident light rays of L light wavelength bands that can be emitted by the illumination unit 1021 or continuous wavelength region including multiple light wavelength bands near this light wavelength band on a wavelength axis.

For example, if the illumination unit 1021 can emit illumination light rays of three RGB colors, the primary color filters in the present embodiment are filters that are configured by two-dimensional arrangement of a filter element which can transmit the R illumination light ray of the incident light rays, a filter element which can transmit the G illumination light ray of the incident light rays, and a filter element which can transmit the B illumination light ray of the incident light rays. When the illumination unit 1021 can emit illumination light rays of four colors R1, R2, G, and B (R1 and R2 are wavelengths which belong to a red wavelength region on the wavelength axis and which are close to each other), the primary color filters in the present embodiment may be configured by two-dimensional arrangement of four kinds of filter elements that can transmit only one of the incident light rays R1, R2, G, and B. However, as a modification, the primary color filters in the present embodiment also include filters configured by two-dimensional arrangement of filter elements that can transmit only one of the light ray in wavelength ranges including the wavelengths of R1 and R2 close to each other on the wavelength axis among the incident light rays, a filter element which can transmit the G illumination light ray of the incident light rays, and a filter element which can transmit the B illumination light ray of the incident light rays.

In the meantime, the "complementary color filters" in the present embodiment are filters that are configured so that filter elements are two-dimensionally arranged to correspond to the positions of the light receiving elements, the filter elements transmitting light ray subtracted one corresponding light wavelength band of L light wavelength bands that can be emitted by the illumination unit 1021 or light ray subtracted the continuous wavelength region including multiple light wavelength bands close to this light wavelength band on the wavelength axis. For example, if the illumination unit 1021 can emit illumination light rays of three RGB colors, the complementary color filters in the present embodiment are filters that are configured by two-dimensional arrangement of a filter element that can transmit a light ray in which the R illumination light ray is subtracted from the incident light rays, a filter element that can transmit a light ray in which the G illumination light ray is subtracted from the incident light rays, and a filter element that can transmit a light ray in which the B illumination light ray is subtracted from the incident light rays. When the illumination unit 1021 can emit illumination light rays of four colors R1, R2, G, and B, the complementary color filters in the present embodiment may be configured by two-dimensional arrangement of four kinds of filter elements that can transmit a light ray in which one of the incident light rays R1, R2, G, and B is subtracted. However, as a modification, the complementary color filters in the present embodiment also include filters configured by two-dimensional arrangement of a filter element that can transmit a light ray subtracted a light lay including the wavelengths of R1 and R2 close to each other on the wavelength axis among the incident light rays, a filter element that can transmit a light ray in which the G illumination light ray is subtracted from the incident light rays, and a filter element that can transmit a light ray in which the G illumination light ray is subtracted from the incident light rays.

Details of the (configuration a) are described below. The emission pattern setting section 1022*b* in the (configuration a) generates an illumination unit control signal so that the illumination light rays of three light wavelength bands are simultaneously emitted in a timing 1 (t=t1), a timing 2 (t=t2), and a timing 3 (t=t3), respectively. The drive pattern generating section 1022*c* generates a light source driver control signal in accordance with the illumination unit control signal and the characteristic information which is stored in the characteristic information storage 1022*a*. The light source driver 1022*d* drives the light sources 1021*a* in accordance with the light source driver control signal.

The imaging section 104 performs imaging synchronously with the illumination of the observation target by the illumination section 102. The color filters 1042*b* in the (configuration a) are primary color filters, so that each filter element only transmits the illumination light ray of the corresponding light wavelength band. That is, the R filter element only transmits the R illumination light ray. Similarly, the G filter element only transmits the G illumination light ray, and the B filter element only transmits the B illumination light ray.

Synchronously with the imaging by the imaging section 104, the A/D converter 1061 samples the image signal from the light receiving elements 1042*a* of the imaging section 104, and converts the sampled image signal into primary image information as a digital signal and then stores the primary image information in the frame memory 1062. In the case of the (configuration a), the primary image information necessary for colorizing, that is, the primary image information including all the three RGB components is stored in the frame memory 1062 by each emission timing of the illumination lights.

The secondary image generation section 1063 identifies the emission pattern (which of the illumination light rays of L light wavelength bands is emitted in each timing) and the presence of the color filters 1042*b* and their kinds (whether the primary color filters or the complementary color filters), and performs image processing for colorizing for primary color information in accordance with the identification result. The secondary image generation section 1063 in the (configuration a) synchronizes (converts into a three-plane form) the primary image information including R information, G information, and B information as the processing for colorizing, and performs processing to generate secondary image information in which each pixel has the R information, the G information, and the B information.

After the image processing by the secondary image generation section 1063, the display mode switch section 1065 outputs the secondary image information generated in the secondary image generation section 1063 to the image correction section 1066. The image correction section 1066 subjects the input secondary image information to correction processing necessary for display in the display 108 and then outputs the information to the display 108. Accordingly, the display 108 displays a color image.

In the (configuration a) described above, the illumination light ray of one light wavelength band enters one light receiving element 1042*a* in emission timing of each illumination light ray. If it is considered that the illumination light rays of L light wavelength bands have the same spectral intensity, the light receiving amount per pixel in each frame in the (configuration a) is equal to the light receiving amount for one light wavelength band.

In the (configuration a), one piece of secondary image information is generated from one piece of primary image information. For example, when three times of imaging are performed with N=3, three pieces of secondary image information are generated from three pieces of primary image information. Here, if it is considered that the number of pixels managed by one light receiving element 1042*a* is "resolution", the resolution in the (configuration a) is one pixel.

Furthermore, in the case of the (configuration a), an image is generated in every timing of the switch of the emission patterns. That is, the extraction time of an image in the (configuration a) corresponds to the switch interval of the emission patterns, and the average velocity of frame display corresponds to the switch velocity of the emission patterns. In FIG. 2, the average velocity of frame display in the (configuration a) is a reference value 1. The purpose is to compare with the other configurations.

Details of the (configuration b) are described below. The emission pattern setting section 1022b in the (configuration b) generates an illumination unit control signal so that the illumination light rays of three light wavelength bands are simultaneously emitted in the timing 1 (t=t1), the timing 2 (t=t2), and the timing 3 (t=t3), respectively. Thus, there is no difference of the illumination light rays applied to the observation target 200 between the (configuration a) and the (configuration b).

Here, the color filters 1042b in the (configuration b) are complementary color filters, and therefore each filter element only transmits the illumination light rays of the corresponding light wavelength band, that is, illumination light rays in which the corresponding illumination light ray is subtracted. In other words, the R complementary color (indicated as R-(bar)) filter element only transmits the R-illumination light ray, that is, G and B illumination light rays. Similarly, the G complementary color (indicated as G-(bar)) filter element only transmits the G-illumination light ray, that is, R and B illumination light rays, and the B complementary color (indicated as B-(bar)) filter element only transmits the B illumination light ray, that is, R and G illumination light rays.

As the processing for colorizing, the secondary image generation section 1063 in the (configuration b) performs a differential calculation of information in which the R-information (i.e. G+B), the G-information (i.e. R+B), and the B-information (i.e. R+G) that are substantially simultaneously acquired are added up, and each of the independent R-, G-, and B-information at a predetermined ratio to synchronize (convert into the three-plane form) image information corresponding to the R information, the G information, and the B information, thereby generating secondary image information.

After the image processing by the secondary image generation section 1063, the display mode switch section 1065 outputs the secondary image information generated in the secondary image generation section 1063 to the image correction section 1066. The image correction section 1066 subjects the input secondary image information to correction processing necessary for display in the display 108 and then outputs the information to the display 108. Accordingly, the display 108 displays a color image.

In the (configuration b) described above, the illumination light rays of (L−1) light wavelength bands enter one light receiving element 1042a. Therefore, the light receiving amount in the light receiving element 1042a per pixel in the frame of the (configuration b) is (L−1) times that in the (configuration a). For example, the light receiving amount is twice when L=3. Thus, the (configuration b) have an advantage over the (configuration a) in the signal-to-noise (SN) ratio. In the (configuration b) as well, one piece of secondary image information is generated from one piece of primary image information. Therefore, the resolution in the (configuration b) is one pixel as in the (configuration a).

Furthermore, in the case of the (configuration b) as well, the number of pieces of primary image information necessary for the generation of an image in the switch interval of the emission patterns are acquired, and secondary image information is generated. That is, the extraction time of an image in the (configuration b) corresponds to the switch interval of the emission patterns, and the average velocity of frame display corresponds to the switch velocity of the emission patterns.

Thus, the (configuration b) is used for higher-sensitivity purposes than the (configuration a). However, the (configuration b) requires processing to convert the complementary color signal to the primary color signal, and is therefore inferior to the (configuration a) in color reproducibility.

Next, the (configuration c) is described with reference to FIG. 3. The (configuration c) is a configuration that uses the emission patterns corresponding to the frame sequential illumination method. In the frame sequential illumination method, the emission pattern setting section 1022b sets an emission pattern so that different illumination light rays among the illumination light rays of L light wavelength bands are applied to the observation target 200 in each of the switch timings of N illumination light rays. Therefore, M=1, and N=L. If the illumination unit 1021 can emit the illumination light rays of three RGB colors, L=3, M=1, and N=3, as shown in FIG. 3.

Details of the (configuration c) are described below. The emission pattern setting section 1022b in the (configuration c) generates an illumination unit control signal so that the R illumination light ray is emitted in the timing 1 (t=t1), the G illumination light ray is emitted in the timing 2 (t=t2), and the B illumination light ray is emitted in the timing 3 (t=t3).

Here, the image pickup device 1042 of the imaging section 104 in the (configuration c) has no color filters 1042b, and has no color selectivity. Therefore, the illumination light ray is not absorbed by the color filters, and is directly received in the light receiving elements 1042a. That is, the R illumination light ray is received by the light receiving elements 1042a in the timing of the emission of the R illumination light ray. Similarly, the G illumination light ray is received by the light receiving elements 1042a in the timing of the emission of the G illumination light ray, and the B illumination light ray is received by the light receiving elements 1042a in the timing of the emission of the B illumination light ray.

The secondary image generation section 1063 in the (configuration c) performs synchronization processing similar to that in the (configuration a). However, in the case of the (configuration c), primary image information necessary for colorizing is prepared by three switches of the illumination light rays. Therefore, the secondary image generation section 1063 in the (configuration c) identifies the switch timing of the illumination light rays by the light source driver control signal, and thus performs synchronization processing (conversion into the three-plane form) at the point where R primary image information 1, G primary image information 2, and B primary image information 3 are prepared, thereby generating secondary image information.

After the image processing by the secondary image generation section 1063, the display mode switch section 1065 outputs the secondary image information generated in the secondary image generation section 1063 to the image correction section 1066. The image correction section 1066 subjects the input secondary image information to correction processing necessary for display in the display 108 and then outputs the information to the display 108. Accordingly, the display 108 displays a color image.

In the (configuration c) described above, the illumination light ray of one light wavelength band enters one light receiving element 1042a in every emission timing of the illumination light ray. However, in the (configuration c), three pieces of primary image information are used to generate one piece of secondary image information, and it can therefore be said that one light receiving element 1042*a* corresponds to L pixels. Accordingly, a light amount per pixel in the (configuration c) is 1/L times (⅓ times in the example) that in the (configuration a), and a light amount per pixel in one frame in the (configuration c) is N/L times (1 time in the example) that in the (configuration a). In the (configuration c), one light receiving element 1042*a* functions as L pixels, so that the spatial resolution is about L times (triple in the example) that in the (configuration a).

Furthermore, the extraction time of an image in the (configuration c) is time which is N times (triple in the example) the switch interval of the emission patterns, and the average velocity of frame display is 1/N times (⅓ times in the example) the switch velocity of the emission patterns.

Thus, the (configuration c) is used for higher-resolution purposes than the (configuration a). However, the (configuration c) is inferior to the (configuration a) in the average velocity of frame display.

Next, the imaging apparatus 100 having the (configuration d) and the (configuration e) is described with reference to FIG. 4. The (configuration d) and the (configuration e) described below "use a light source which can apply multiple colors to the observation target to set multiple emission patterns to extract and emit not only one color but also predetermined multiple colors, and switch and emit multiple sets of emission patterns having different combinations of illumination colors". Display performance is improved by such switching of the emission patterns.

Details of the (configuration d) are described below. In the (configuration d), the image pickup device 1042 has no color filters 1042*b* in the imaging apparatus 100 in which N sets of emission patterns are prepared to extract illumination light rays of M light wavelength bands from illumination light rays of L light wavelength bands and then emit the illumination light rays and which sequentially switches the N sets of emission patterns. In the example described below, N=L=3 and M=2.

The emission pattern setting section 1022*b* in the (configuration d) generates an illumination unit control signal so that the G and B illumination light rays are emitted as a pattern A1 in the timing 1 (t=t1), the R and B illumination light rays are emitted as a pattern A2 in the timing 2 (t=t2), and the R and G illumination light rays are emitted as a pattern A3 in the timing 3 (t=t3).

The image pickup device 1042 in the (configuration d) has no color filters 1042*b*. Therefore, the illumination light ray is not absorbed by the color filters, and is directly received in the light receiving elements 1042*a*. That is, the G and B illumination light rays are received by the light receiving elements 1042*a* in the timing of the emission of the G and B illumination light rays. This is similar to the reception of the R-illumination light ray in the light receiving elements 1042*a*. Similarly, the R and B illumination light rays are received by the light receiving elements 1042*a* in the timing of the emission of the R and B illumination light rays. This is similar to the reception of the G-illumination light ray in the light receiving elements 1042*a*. Moreover, the R and G illumination light rays are received by the light receiving elements 1042*a* in the timing of the emission of the R and G illumination light rays. This is similar to the reception of the B-illumination light ray in the light receiving elements 1042*a*.

The secondary image generation section 1063 in the (configuration d) performs a combination of image processing in the (configuration b) and the (configuration c). That is, the secondary image generation section 1063 generates secondary image information from three pieces of primary image information as in the (configuration c). However, in the case of the (configuration d), primary image information 1, 2, and 3 including complementary color information are obtained. Therefore, the secondary image generation section 1063 in the (configuration d) performs a differential calculation of information in which all the primary image information 1, 2, and 3 including the R-information, the G-information, and B-information are added, and each of the independent R-, G-, and B-information at a predetermined ratio to synchronize (convert into the three-plane form) image information corresponding to the R information, the G information, and the B information, thereby generating secondary image information, as in the (configuration b).

After the image processing by the secondary image generation section 1063, the display mode switch section 1065 outputs the secondary image information generated in the secondary image generation section 1063 to the image correction section 1066. The image correction section 1066 subjects the input secondary image information to correction processing necessary for display in the display 108 and then outputs the information to the display 108. Accordingly, the display 108 displays a color image.

In the (configuration d) described above, the illumination light rays of two light wavelength bands enter one light receiving element 1042*a* in every switch timing of the illumination light rays. Therefore, in one frame, a light amount per pixel in the (configuration d) is twice that in the (configuration a). More generally, the illumination light rays of M light wavelength bands enter one light receiving element 1042*a* in every switch timing of the illumination light rays. Therefore, a light amount per pixel in the (configuration d) is M times that in the (configuration a) on the time average. However, one light receiving element 1042*a* corresponds to L pixels, so that a light amount per pixel is M/L times, and a light amount per pixel in one frame is N×M/L times. In the (configuration d), one light receiving element 1042*a* functions as L pixels, so that the spatial resolution is L times that in the (configuration a).

Furthermore, the extraction time of an image in the (configuration d) is time which is triple the switch interval of the emission patterns, and the average velocity of frame display is ⅓ times the switch velocity of the emission patterns. In general, the extraction time of an image in the (configuration d) is time which is N times the switch interval of the emission patterns, and the average velocity of frame display is 1/N times the switch velocity of the emission patterns.

Thus, the (configuration d) is used for higher-sensitivity and higher-resolution purposes than the (configuration a). However, the (configuration d) is inferior to the (configuration a) in the average velocity of frame display. On the other hand, the (configuration d) has the advantage of having the same level of resolution as the (configuration c) which has high resolution and also having higher sensitivity than that of the (configuration c).

Details of the (configuration e) are described below. In the (configuration e), the image pickup device 1042 has primary color filters in the imaging apparatus 100 in which N sets of emission patterns are prepared to extract illumination light rays of M light wavelength bands from illumination light rays of L light wavelength bands and then emit the illumination light rays and which sequentially switches the N sets of emission patterns. In the example described below, N=L=3 and M=2.

As in the (configuration d), the emission pattern setting section 1022*b* in the (configuration e) generates an illumination unit control signal so that the G and B illumination light rays are emitted as the pattern A1 in the timing 1 (t=t1), the R and B illumination light rays are emitted as the pattern A2 in the timing 2 (t=t2), and the R and G illumination light rays are emitted as the pattern A3 in the timing 3 (t=t3).

The imaging section 104 in the (configuration e) has primary color filters. Therefore, the illumination light corresponding to each filter element is only received in the light receiving element 1042a. That is, in the timing of the emission of the G and B illumination light rays, the R filter element does not transmit any illumination light ray, the G filter element only transmits the G illumination light ray, and the B filter element only transmits the B illumination light ray. In the timing of the emission of the R and B illumination light rays, the R filter element only transmits the R illumination light ray, the G filter element does not transmit any illumination light ray, and the B filter element only transmits the B illumination light ray. In the timing of the emission of the R and G illumination light rays, the R filter element only transmits the R illumination light ray, the G filter element only transmits the G illumination light ray, and the B filter element does not transmit any illumination light ray. Thus, in the (configuration e), information regarding primary colors corresponding to different two sets of color components is obtained in each timing.

The secondary image generation section 1063 in the (configuration d) generates secondary image information from the information regarding the primary colors obtained in successive two timings. That is, the secondary image generation section 1063 generates secondary image information by performing processing to synchronize (convert into the three-plane form) the G information and the B information obtained in the timing 1 and the R information obtained in the timing 2. The secondary image generation section 1063 also generates secondary image information by performing processing to synchronize (convert into the three-plane form) the B information obtained in the timing 1 and the R information and the G information obtained in the timing 3.

After the image processing by the secondary image generation section 1063, the display mode switch section 1065 outputs the secondary image information generated in the secondary image generation section 1063 to the image correction section 1066. The image correction section 1066 subjects the input secondary image information to correction processing necessary for display in the display 108 and then outputs the information to the display 108. Accordingly, the display 108 displays a color image.

In the (configuration e) described above, the illumination light ray of one light wavelength band enters one light receiving element 1042a in every switch timing of the illumination light rays. However, a light amount per pixel in one frame is smaller than that in the (configuration a). In the (configuration e), one light receiving element 1042a functions as one pixel, so that the spatial resolution is similar to that in the (configuration a).

Furthermore, the extraction time of an image in the (configuration e) is time which is twice the switch interval of the emission patterns, and the average velocity of frame display is ½ times the switch velocity of the emission patterns. In general, the extraction time of an image in the (configuration e) is time which is (N−1) times the switch interval of the emission patterns, and the average velocity of frame display is 1/(N−1) times the switch velocity of the emission patterns.

Thus, the (configuration e) is used in a mode of a higher frame rate than the (configuration c).

In the (configuration d) and the (configuration e) in this example described here, N=L=3 and M=2. However, L, M, and N are not exclusively set as shown in the example. For example, the number of emission patterns may be N=4 so that all the illumination light rays of three light wavelength bands are emitted in one of four emission patterns.

Next, the imaging apparatus 100 having the (configuration f) is described with reference to FIG. 5. Similarly to the (configuration d), the (configuration e), and the (configuration f) described below "uses a light source which can apply multiple colors to the observation target to set multiple emission patterns to extract and emit not only one color but also predetermined multiple colors, and switch and emit multiple sets of emission patterns having different combinations of illumination colors". In this configuration, the image pickup device 1042 has complementary color filters. The (configuration f) can be further classified into a (configuration f1) to a (configuration f6). Details of the (configuration f1) to the (configuration f6) in the case of L=N=3 and M=2 are described below.

The emission pattern setting section 1022b in the (configuration f1) to the (configuration f6) generates an illumination unit control signal so that the G and B illumination light rays are emitted as the pattern A1 in the timing 1 (t=t1), the R and B illumination light rays are emitted as the pattern A2 in the timing 2 (t=t2), and the R and G illumination light rays are emitted as the pattern A3 in the timing 3 (t=t3).

The imaging section 104 in the (configuration f1) to the (configuration f6) has the complementary color filters. Therefore, the illumination light ray in which the illumination light ray corresponding to each filter element is subtracted is only received in the light receiving element 1042a. That is, in the timing of the emission of the G and B illumination light rays, the R-filter element transmits the G and B illumination light rays as they are, the G-filter element only transmits the B illumination light ray, and the B-filter element only transmits the G illumination light ray. In the timing of the emission of the R and B illumination light rays, the R-filter element only transmits the B illumination light ray, the G-filter element transmits the R and B illumination light rays as they are, and the B-filter element only transmits the R illumination light ray. In the timing of the emission of the R and G illumination light rays, the R-filter element only transmits the G illumination light ray, the G-filter element only transmits the R illumination light ray, and the B-filter element transmits the R and B illumination light rays as they are.

Details of the (configuration f1) are described below. In the timing 1 (t=t1), the secondary image generation section 1063 in the (configuration f1) performs processing to recognize a signal obtained by the light receiving element 1042a corresponding to the R-filter element as an R complementary color signal, recognize a signal obtained by the light receiving element 1042a corresponding to the G-filter element as a B primary color signal, and recognize a signal obtained by the light receiving element 1042a corresponding to the B-filter element as a G primary color signal, and then use image information including the above information as the primary image information 1 to generate secondary image information 1. In the timing 2 (t=t2), the secondary image generation section 1063 performs processing to recognize a signal obtained by the light receiving element 1042a corresponding to the R-filter element as a B primary color signal, recognize a signal obtained by the light receiving element 1042a corresponding to the G-filter element as a G complementary color signal, and recognize a signal obtained by the light receiving element 1042a corresponding to the B-filter element as an R primary color signal, and then use image information including the above information as the primary image information 2 to generate secondary image information 2. In the timing 3 (t=t3), the secondary image generation section 1063 performs processing to recognize a signal obtained by the light receiving element 1042a corresponding to the R-filter element as a G primary color signal, recognize a signal obtained by the light receiving element 1042a corresponding to the G-filter element as an R primary color signal, and recognize a signal obtained by the light receiving element 1042a corresponding to the B-filter element as a B complementary color signal, and then use image information including the above information as the primary image information 3 to generate secondary image information 3.

The secondary image generation section 1063 in the (configuration f1), for example, takes a difference between the sum of the RGB primary color signals obtained by the light emission using the emission pattern which is one or two emission patterns before in terms of time and each of the complementary color signals at t=t1, t2, and t3 while repeating the switch of the emission patterns, and thereby performs a pseudo-conversion of each complementary color signal into a primary color signal and then performs synchronization (conversion into the three-plane form). It is also possible to take a difference between not the sum of the RGB primary color signals but the sum of the complementary color signals and the complementary color signals at t=t1, t2, and t3. In this case, a difference is taken between ½ of the sum of the RGB complementary color signals and the complementary color signals at t=t1, t2, and t3.

After the image processing by the secondary image generation section 1063, the display mode switch section 1065 outputs the secondary image information generated in the secondary image generation section 1063 to the image correction section 1066. The image correction section 1066 subjects the input secondary image information to correction processing necessary for display in the display 108 and then outputs the information to the display 108. Accordingly, the display 108 displays a color image.

In the (configuration f1) described above, one light receiving element functions as one pixel, as in the (configuration a). Therefore, the spatial resolution in the (configuration f1) is the same as that in the (configuration a). On the other hand, the amount of light received per pixel is about (L+M−1)/L times that in the (configuration a) on the time average (e.g. ⅔ times in the case of L=N=3 and M=2). The light receiving amount per pixel in one frame is also (L+M−1)/L times that in the (configuration a).

Furthermore, in the case of the (configuration f1), the number of pieces of primary image information necessary for the generation of an image in the switch interval of the emission patterns are acquired, and secondary image information is generated. Therefore, the substantial average velocity of frame display is close to that in the (configuration a), and is about N times that in the (configuration c).

Thus, the (configuration f1) is used in a mode of higher sensitivity than the (configuration a) and a higher frame rate than the (configuration c).

Details of the (configuration f2) are described below. The (configuration f2) is the same as the (configuration f1) up to the acquisition of the secondary image information, and is different in that tertiary image information is generated as a display image. That is, the secondary image generation section 1063 in the (configuration f2) inputs three pieces of most recent secondary image information 1, 2, and 3 to the tertiary image generation section 1064. The tertiary image generation section 1064 composes the secondary image information 1, 2, and 3 to generate one piece of tertiary image information including information regarding all the RGB light wavelength bands. The display mode switch section 1065 outputs the tertiary image information generated in the tertiary image generation section 1064 to the image correction section 1066. The image correction section 1066 subjects the input tertiary image information to correction processing necessary for display in the display 108 and then outputs the information to the display 108. Accordingly, the display 108 displays a color image. Although not described in detail here, the primary image information 1, 2, and 3 and the secondary image information 1, 2, and 3 may be used to generate the tertiary image information including information regarding all the RGB light wavelength bands.

In the (configuration f2) described above, three pieces of primary image information are used to generate one piece of secondary image information, as in the (configuration c). That is, in the (configuration f2) as well, one light receiving element functions as L pixels, so that the spatial resolution is L times that in the (configuration a). On the other hand, the average velocity of frame display is 1/N times that in the (configuration a). The (configuration f2) is similar to the (configuration f1) in other respects.

Details of the (configuration f3) are described below. The (configuration f3) is similar to the (configuration f2) up to the generation of the tertiary image information. After the generation of the tertiary image information, the display mode switch section 1065 in the (configuration f3) selects one of the secondary image information generated in the secondary image generation section 1063 and the tertiary image information generated in the tertiary image generation section 1064 as a final display frame and then outputs the selected one to the image correction section 1066. The image correction section 1066 subjects the input secondary image information to correction processing necessary for display in the display 108 and then outputs the information to the display 108. Accordingly, the display 108 displays a color image. As described above, three pieces of most recent secondary image information are used to generate the tertiary image information. Therefore, the display mode switch section 1065 selects image information in and after the third frames. Although one of the image based on the secondary image information and the image based on the tertiary image information is displayed in the example described here, both the images may be displayed in parallel.

In the (configuration f3) described above, it is possible to switch between an image display mode corresponding to the (configuration f1) and an image display mode corresponding to the (configuration f2) as needed. That is, it is possible to display with image characteristics (high resolution but a low frame rate) of the (configuration f2) when high resolution is required, and display with image characteristics (not high resolution but a high frame rate) of the (configuration f1) when the rapid motion of the observation target is to be smoothly displayed. As described above, whether to give priority to the resolution or the frame rate can be selected in accordance with the image display mode, or both the modes can be used together for simultaneous display. This is a specific advantageous effect obtained by a combination of the image pickup device having the color filters and the light source which switches and emits the emission patterns to simultaneously emit lights of multiple light wavelength bands. This advantage is not obtained by a combination of the white light broadband illumination method and the image pickup device having the color filters or a combination of the monochromatic frame sequential illumination method and the image pickup device having no color filters.

Details of the (configuration f4) are described below. The (configuration f4) is similar to the (configuration f1) up to the acquisition of the primary image information. The secondary image generation section 1063 in the (configuration f4) performs processing to recognize a signal obtained by the light receiving element 1042*a* corresponding to the G-filter element acquired in the timing 1 (t=t1) as a B primary color signal, recognize a signal obtained by the light receiving element 1042*a* corresponding to the B-filter element as a G primary color signal, and recognize a signal obtained by the light receiving element 1042*a* corresponding to the R-filter element acquired in the timing 2 (t=t2) as an R primary color signal, and then use image information including the above information as the primary image information 1 to generate secondary image information 1. The secondary image generation section 1063 also performs processing to recognize a signal obtained by the light receiving element 1042*a* corresponding to the R-filter element acquired in the timing 1 (t=t1) as an R complementary color signal, recognize a signal obtained by the light receiving element 1042*a* corresponding to the G-filter element acquired in the timing 2 (t=t2) as a G complementary color signal, and recognize a signal obtained by the light receiving element 1042*a* corresponding to the B-filter element acquired in the timing 3 (t=t3) as a B complementary color signal, and then use image information 1 including the above information as the primary image information 2 to generate secondary image information 2. Further, the secondary image generation section 1063 performs processing to recognize a signal obtained by the light receiving element 1042*a* corresponding to the R-filter element acquired in the timing 2 (t=t2) as a B primary color signal, recognize a signal obtained by the light receiving element 1042*a* corresponding to the R-filter element acquired in the timing 3 (t=t3) as a G primary color signal, and recognize a signal obtained by the light receiving element 1042*a* corresponding to the G-filter element acquired in the timing 3 (t=t3) as an R complementary color signal, and then use image information including the above information as the primary image information 3 to generate secondary image information 3.

The primary image information obtained in the (configuration f4) has one of the primary color information for the RGB light wavelength bands and the complementary color information for the RGB light wavelength bands. Therefore, each of the pieces of the secondary image information 1, 2, and 3 can be sent to the image correction section 1066 and further to the display 108 without passing through the tertiary image generation section 1064. When image processing is performed with the primary color signals alone for the simplification of the image processing, the secondary image generation 3 may not be used to generate the final image in some cases. In the following explanation of the advantageous effects of the (configuration f4), the advantageous effects of the case in which the secondary image generation 3 is not used to generate the final image are not described.

In the (configuration f4) described above, one light receiving element 1042*a* functions as one pixel, so that the spatial resolution is the same as that in the (configuration a). When the switch of the emission patterns A1 to A3 is completed, the secondary image information that can be used as it is for display and recorded is acquired, the average velocity of frame display is the same as that in the (configuration a), that is, N times that in the (configuration c). On the other hand, the amount of light received per pixel is about (L+M−1)/L times that in the (configuration a) on the time average. The light receiving amount per pixel in one frame is also (L+M−1)/L times that in the (configuration a).

Details of the (configuration f5) are described below. The (configuration f5) is similar to the (configuration f4) up to the generation of the secondary image information, and is different in that tertiary image information is generated as a display image. That is, the secondary image generation section 1063 in the (configuration f5) inputs three pieces of most recent secondary image information 1, 2, and 3 to the tertiary image generation section 1064. The tertiary image generation section 1064 composes the secondary image information 1, 2, and 3 to generate one piece of tertiary image information including information regarding all the RGB light wavelength bands. The display mode switch section 1065 outputs the tertiary image information generated in the tertiary image generation section 1064 to the image correction section 1066. The image correction section 1066 subjects the input tertiary image information to correction processing necessary for display in the display 108 and then outputs the information to the display 108. Accordingly, the display 108 displays a color image.

In the (configuration f5) described above, one light receiving element 1042*a* functions as L pixels, so that the spatial resolution increases L times that in the (configuration a). Only one tertiary image information is composed and acquired as an image for the switch of the emission patterns A1 to A3, so that the average velocity of frame display is 1/N times that in the (configuration a), that is, on the same level as that in the (configuration c). On the other hand, the amount of light received per pixel increases about (L+M−1)/L times that in the (configuration a) on the time average. The light receiving amount per pixel in one frame is also about (L+M−1)/L times that in the (configuration a).

Details of the (configuration f6) are described below. The (configuration f6) is similar to the (configuration f5) up to the generation of the tertiary image information. After the generation of the tertiary image information, the display mode switch section 1065 selects one of the secondary image information generated in the secondary image generation section 1063 and the tertiary image information generated in the tertiary image generation section 1064 as a final display frame and then outputs the selected one to the image correction section 1066. The image correction section 1066 subjects the input image information to correction processing necessary for display in the display 108 and then outputs the information to the display 108. Accordingly, the display 108 displays a color image. As described above, three pieces of most recent secondary image information are used to generate the tertiary image information. Therefore, the display mode switch section 1065 selects image information in and after the third frames. Although one of the image based on the secondary image information and the image based on the tertiary image information is displayed in the example described here, both the images may be displayed in parallel.

In the (configuration f6) described above, it is possible to switch between an image display mode corresponding to the (configuration f4) and an image display mode corresponding to the (configuration f5) as needed. That is, it is possible to display with image characteristics (high resolution but a low frame rate) of the (configuration f5) when high resolution is required, and display with image characteristics (not high resolution but a high frame rate) of the (configuration f4) when the rapid motion of the observation target is to be smoothly displayed. As described above, whether to give priority to the resolution or the frame rate can be selected in accordance with the image display mode, or both the modes can be used together for simultaneous display. This is a specific advantageous effect obtained by a combination of the image pickup device having the color filters and the light source which switches and emits the emission patterns to simultaneously emit lights of multiple light wavelength bands. This advantage is not obtained by a combination of the white light broadband illumination method and the image pickup device having the color filters or a combination of the monochromatic frame sequential illumination method and the image pickup device having no color filters.

As a modification of the (configuration f1) to the (configuration f6), the number of emission patterns may be N=4, and one of the emission patterns may be an emission pattern A0 which simultaneously emits illumination light rays of three light wavelength bands. In this case, information regarding complementary colors in the primary image information obtained in, for example, the (configuration f1) can be converted into information regarding primary colors by taking a difference between ½ of a total of the signals received in three light receiving elements 1042a of a full band (RGB) and the complementary color signal acquired in each of the timings 1, 2, and 3.

As described above, according to the present embodiment, emission patterns are set in accordance with the characteristics of the imaging section 104 and performance required for the imaging apparatus 100, so that it is possible to prevent the size increase of the apparatus and also select the basic performance of the imaging apparatus as needed.

[Modifications]

Next, modifications of the present embodiment are described. In the example according to the embodiment described above, the number L of the light wavelength bands that can be emitted by the illumination section 102 is 3. However, L is not limited to 3. In an example described in a second embodiment, L=4. FIG. 6 shows an example of emission patterns and filter arrangement in the case of L=4, N=4, and M=2. Emission patterns B1 to B4 shown in the upper part of FIG. 6 are emission patterns which extract and emit illumination light rays of different two light wavelength bands from illumination light rays of four light wavelength bands, respectively (i.e. M=2). In this case, the emission pattern setting section 1022b generates an illumination unit control signal so that the G and B illumination light rays are emitted as the pattern B1 in the timing 1 (t=t1), the R and orange (O) illumination light rays are emitted as the pattern B2 in the timing 2 (t=t2), the R and G illumination light rays are emitted as the pattern B3 in the timing 3 (t=t3), and the O and R illumination light rays are emitted as the pattern B4 in a timing 4 (t=t4). That is, the pattern A2 shown in the (configuration d), the (configuration e), and the (configuration f) is classified into the pattern B2 and the pattern B4.

Emission patterns C1 to C4 shown in the upper part of FIG. 6 are emission patterns which extract and emit illumination light rays of different three light wavelength bands from illumination light rays of four light wavelength bands, respectively (i.e. M=3). In this case, the emission pattern setting section 1022b generates an illumination unit control signal so that the G, B, and O illumination light rays are emitted as the pattern C1 in the timing 1 (t=t1), the R, G, and B illumination light rays are emitted as the pattern C2 in the timing 2 (t=t2), the R, B, and O illumination light rays are emitted as the pattern C3 in the timing 3 (t=t3), and the R, G, and O illumination light rays are emitted as the pattern C4 in the timing 4 (t=t4).

Emission patterns D0 to D4 shown in the upper part of FIG. 6 are formed by the addition of the emission pattern D0 which emits all the RGBO illumination light rays to the emission patterns B1 to B4. In this case, the emission pattern setting section 1022b generates an illumination unit control signal so that the R, G, B, and O illumination light rays are emitted as the pattern D0 in a timing 0 (t=t0), the G and B illumination light rays are emitted as the pattern D1 in the timing 1 (t=t1), the B and O illumination light rays are emitted as the pattern D2 in the timing 2 (t=t2), the B and O illumination light rays are emitted as the pattern D3 in the timing 3 (t=t3), and the R and O illumination light rays are emitted as the pattern D4 in the timing 4 (t=t4).

The lower part of FIG. 6 shows the arrangement of the filters. A four-primary-color filter shown in the lower part of FIG. 6 is a filter configured by two-dimensional arrangement of a filter element that can transmit one corresponding light among incident light rays of four light wavelength bands that can be emitted by the illumination unit 1021. That is, this primary color filter is a filter configured by two-dimensional arrangement of a filter element that can transmit the R illumination light ray among the incident light rays, a filter element that can transmit the G illumination light ray among the incident light rays, a filter element that can transmit the B illumination light ray among the incident light rays, and a filter element that can transmit the O illumination light ray among the incident light rays. On the other hand, a four-complementary-color filter shown in the lower part of FIG. 6 is a filter configured by two-dimensional arrangement of a filter element that can transmit light rays in which one corresponding illumination light ray is subtracted from among lights of L light wavelength bands that can be emitted by the illumination unit 1021. That is, this complementary color filter is a filter configured by two-dimensional arrangement of a filter element that can transmit light rays in which the R illumination light ray is subtracted from the incident light rays, a filter element that can transmit light rays in which the G illumination light ray is subtracted from the incident light rays, a filter element that can transmit light rays in which the B illumination light ray is subtracted from the incident light rays, and a filter element that can transmit light rays in which the O illumination light ray is subtracted from the incident light rays.

Even the configuration shown in FIG. 6 is similar in the basic operation and advantageous effects to the (configuration d) to the (configuration f). Details are not described.

While the present invention has been described above on the basis of the embodiments, it should be understood that the present invention is not limited to the embodiments described above, and various modifications and applications can be made within the spirit of the present invention.

In the above explanation, the switch setting of illumination patterns is fixed (i.e. M is fixed) in each of the cases of the (configuration a) to the (configuration c) (switch illumination of one band/pattern) and the (configuration d) and the (configuration f) (switch illumination of multiple bands/patterns) as illumination patterns, and then an image processing algorithm of corresponding image processing means is shown, and image characteristics that can be generated by this algorithm and its switch variations are described. However, the following configuration is also included as a modification: the setting of illumination switch patterns is changed in terms of time (e.g. by switching from M=1 to M=2), and a corresponding image processing algorithm is used to obtain different image characteristics. For example, for the same configuration of the imaging section, it is possible to "switch a set of 'the illumination pattern and the image processing algorithm' described in the (configuration c) and the (configuration d) to obtain multiple image characteristics", and it is also possible to "switch a set of 'the illumination pattern and the image processing algorithm' described in the (configuration b) and the (configuration f) to obtain multiple image characteristics".

The number L of the light wavelength bands that can be emitted by the illumination unit does not need to be the same as the number of primary color filters or complementary color filters. By way of example, one primary color filter shown in FIG. 6 may be reduced so that three kinds of filters: the RO filter, the G filter, and the B filter are arranged. (The RO filter only transmits the R and O light rays, and blocks G and B. The G filter only transmits G. The B filter only transmits B.). Similarly, one complementary color filter shown in FIG. 6 may be reduced so that three kinds of filters: the RO-filter, the G-filter, and the B-filter are arranged. (The RO-filter blocks the R and O light rays, and transmits G and B. The G filter only blocks G. The B filter only blocks B.).

In the configuration and the embodiment of the (configuration d) to the (configuration f), the image pickup device of the imaging section in the following cases have been described: "the cases in which the filter arrangement combined with the light receiving element arrangement is a monochromatic filter, a complementary color filter, and a primary color filter". However, the following case is also included: the image pickup device is configured so that light wavelength sensitivity characteristics are a predetermined arrangement without even being combined with filters (i.e. each pixel of the image pickup device has different light wavelength sensitivity characteristics). In the present specification, the "light receiving element" means "a light detection element which does not particularly limit sensitivity characteristics with regard to the light wavelength", the "imaging pixel" means "a light detection element which includes sensitivity characteristics with regard to the light wavelength", and the "image pickup device" means an assembly of arrangements of the "imaging pixels (light detection elements including sensitivity characteristics with regard to the light wavelength)".

What is claimed is:

1. An imaging apparatus comprising:
    an illumination unit configured to selectively apply illumination light rays of light wavelength bands different from each other to an observation target;
    an illumination switch controller configured to control the illumination unit so that the illumination light rays are sequentially emitted from the illumination unit in sets of emission patterns different from each other based on an illumination unit control signal;
    an imaging section which comprises an image pickup device where imaging pixels having a predetermined arrangement and having predetermined light wavelength sensitivity characteristics are disposed, the imaging section being configured to image the observation target by the image pickup device to acquire an image signal regarding the observation target;
    an imaging mode controller configured to acquire required performance information concerning the imaging section; and
    an image processor configured to process the image signal,
    wherein the illumination switch controller is configured to generate the illumination unit control signal corresponding to each of the sets of emission patterns based on arrangement information in the light wavelength sensitivity characteristics of the imaging pixels of the imaging section and the required performance information, and
    wherein the image processor processes the image signal based on the illumination unit control signal and the arrangement information in the light wavelength sensitivity characteristics of the imaging pixels of the imaging section.

2. The imaging apparatus according to claim 1,
    wherein one or more kinds of the required performance information are supplied to the imaging mode controller,
    the imaging mode controller instructs the illumination unit to switch a setting of the illumination unit control signal to correspond to the one or more kinds of the required performance information, and switches a setting of an image processing algorithm for the image processor, and
    the image processor switches or simultaneously generates image signals having multiple image characteristics.

3. The imaging apparatus according to claim 1,
    wherein $L \geq 3$, and $2 \leq M \leq L$, and $N \geq 2$,
    in which L is the number of light wavelength bands of illumination light rays emittable by the illumination unit,
    M is the number of light wavelength bands of illumination lights emittable by the same set of emission patterns, and
    N is the number of emission patterns.

4. The imaging apparatus according to claim 3, wherein $L=N \geq 3$, and $M=L-1$.

5. The imaging apparatus according to claim 3, wherein the imaging section comprises
    the image pickup device configured by the arrangement of light receiving elements which convert an optical image of the observation target into the image signal and the arrangement of color filters combined with the light receiving elements, and
    a complementary color filter in which the color filters are arranged so that the light receiving elements transmit the optical image of a wavelength band having a complementary color relation with each of light wavelength bands of L illumination light rays emittable by the illumination unit, and
    the image processor processes the image signal based on timing of switching the illumination unit control signal to acquire an image.

6. The imaging apparatus according to claim 5,
    wherein the image processor recognizes that the image signal obtained from the light receiving element in which the number of wavelength bands of the optical image transmitted by the complementary color filter that is recognized from the timing of switching the illumination unit control signal is M−1 is a primary color signal corresponding to wavelength bands of M−1 optical images transmitted by the complementary color filter.

7. The imaging apparatus according to claim 6,
    wherein the image processor recognizes that the image signal obtained from the light receiving element in which the number of wavelength bands of the optical image transmitted by the complementary color filter that is recognized from the timing of switching the illumination unit control signal is M is a complementary color signal corresponding to wavelength bands of M optical images transmitted by the complementary color filter.

8. The imaging apparatus according to claim 7,
wherein the image processor processes a combination of the image signal recognized as a primary color signal and the image signal recognized as a complementary color signal.

9. The imaging apparatus according to claim 8,
wherein the required performance information includes information indicating that the imaging apparatus is set to a high frame rate mode, and
when the required performance information is the information indicating that the imaging apparatus is set to the high frame rate mode, the image processor performs a predetermined calculation for primary image information in which the image signal recognized as the primary color signal and the image signal recognized as the complementary color signal are mixed to generate secondary image information in emission timing corresponding to each of N sets of emission patterns.

10. The imaging apparatus according to claim 9,
wherein as the predetermined calculation, the image processor performs a calculation to convert the image signal recognized as the complementary color signal mixed in the primary image information into the image signal which is recognized as a primary color signal, or a calculation to convert the image signal recognized as the primary color signal mixed in the primary image information into the image signal which is recognized as a complementary color signal.

11. The imaging apparatus according to claim 10,
wherein the calculation to convert the image signal recognized as the complementary color signal into the image signal which is recognized as the primary color signal is a calculation to convert each complementary color signal into a primary color signal by a calculation of a sum of primary color signals corresponding to L light bands of the previous emission pattern in a time series and a complementary color signal obtained by the emission of each set of illumination patterns.

12. The imaging apparatus according to claim 10,
wherein the emission patterns include an emission pattern to perform simultaneous illumination of illumination lights of L light wavelength bands, and
the calculation to convert the image signal recognized as the complementary color signal into the image signal which is recognized as the primary color signal is a calculation to convert each complementary color signal into the primary color signal by a calculation of an image signal corresponding to an amount of light received in the imaging section in the emission pattern to perform the simultaneous illumination and a complementary color signal obtained by the emission of each set of illumination patterns.

13. The imaging apparatus according to claim 8,
wherein an image signal in which primary color signals and complementary color signals obtained by the imaging section in each of N sets of emission patterns are mixed is primary color information, and
the image processor composes at least one of a set of primary color signals corresponding to light wavelength bands different from each other obtained by the imaging section in successive timings in response to switch of the emission patterns and a set of complementary color signals corresponding to light wavelength bands different from each other obtained by the imaging section in successive timings in response to the switch of the emission patterns to generate secondary image information.

14. The imaging apparatus according to claim 9,
wherein the image processor further composes N sets of secondary image information obtained for N sets of successive emission patterns to generate tertiary image information.

15. The imaging apparatus according to claim 14,
wherein the image processor comprises a display mode switch section which selects one or both of the secondary image information and the tertiary image information as image information for display.

16. The imaging apparatus according to claim 3,
wherein in the imaging section, the imaging pixel having the predetermined arrangement and having the predetermined light wavelength sensitivity characteristics has light receiving sensitivity to any one of the light wavelength bands of L illumination lights emittable by the illumination unit, and
the image processor recognizes an image signal output from the light receiving element of the imaging section synchronously with switching of the illumination unit control signal as complementary color signals of illumination colors of N sets of emission patterns in which combinations of illumination light rays are different from each other, uses a set of image signals from L closely disposed light receiving elements as N sets of primary image information, and composes the N sets of primary image information to generate secondary image information.

17. The imaging apparatus according to claim 3, wherein the imaging section comprises
the image pickup device configured by the arrangement of light receiving elements which convert an optical image of the observation target into the image signal and the arrangement of color filters combined with the light receiving elements, and
a primary color filter in which the color filters are arranged so that the light receiving elements transmit the optical image of a wavelength band having a primary color relation with each of light wavelength bands of L illumination light rays emittable by the illumination unit, and
the image processor composes a set of primary color signals corresponding to light wavelength bands different from each other obtained from the imaging section in successive timings in response to switching of the emission patterns with N sets of primary image information including a primary color signal obtained from the imaging section for each of N sets of emission patterns to generate secondary image information.

18. The imaging apparatus according to claim 1, wherein $\lambda Lw, i < \lambda Fw, i$,
in which $\lambda Lw, i$ ($i=1, 2, \ldots, L$) is the wavelength band width of light rays of L wavelength bands emittable by the illumination unit, and $\lambda Fw, i$ ($i=1, 2, \ldots, L$) is a wavelength band width detectable in the imaging section.

19. The imaging apparatus according to claim 18, wherein the illumination unit emits some or all of the illumination lights by using a laser or a superluminescent diode.

20. The imaging apparatus according to claim 1,
wherein the acquisition of the image by the imaging section and the illumination of the observation target by the illumination unit are performed in an environment in which outside light applied to the observation target is effectively negligible for the illumination light applied to the observation target from the illumination unit, and the environment in which the outside light applied to the observation target is effectively negligible for the illumination light applied to the observation target from the illumination unit is an environment in which the entrance of the outside light into the imaging section is inhibited or an environment in which components of the outside light are cancelable from the image signal acquired in the imaging section or components of the illumination light are extractable.

21. A microscope apparatus comprising the imaging apparatus according to claim 1.

22. An endoscope apparatus comprising the imaging apparatus according to claim 1.

* * * * *